(12) United States Patent
Bono et al.

(10) Patent No.: US 12,035,922 B2
(45) Date of Patent: Jul. 16, 2024

(54) BI-DIRECTIONAL DISK REMOVAL AND DECORTICATION TOOL

(71) Applicant: GLOBUS MEDICAL, INC., Audubon, PA (US)

(72) Inventors: Peter L. Bono, Bingham Farms, MI (US); James D. Lark, Troy, MI (US); John S. Scales, Clinton Township, MI (US); Anthony J. Ruhala, Almont, MI (US)

(73) Assignee: Globus Medical, Inc., Audubon, PA (US)

( * ) Notice: Subject to any disclaimer, the term of this patent is extended or adjusted under 35 U.S.C. 154(b) by 2 days.

(21) Appl. No.: 17/719,879

(22) Filed: Apr. 13, 2022

(65) Prior Publication Data

US 2022/0338881 A1 Oct. 27, 2022

Related U.S. Application Data

(60) Provisional application No. 63/180,444, filed on Apr. 27, 2021.

(51) Int. Cl.
*A61B 17/16* (2006.01)
*A61B 17/32* (2006.01)
*A61B 17/00* (2006.01)

(52) U.S. Cl.
CPC .......... *A61B 17/1615* (2013.01); *A61B 17/32* (2013.01); *A61B 2017/00477* (2013.01)

(58) Field of Classification Search
CPC .............. A61B 17/1615; A61B 17/164; A61B 17/1671
See application file for complete search history.

(56) References Cited

U.S. PATENT DOCUMENTS

| | | | | |
|---|---|---|---|---|
| 6,425,887 B1 * | 7/2002 | McGuckin | ......... | A61B 17/1671 604/272 |
| 9,962,170 B2 * | 5/2018 | Jansen | ............... | A61B 17/1622 |
| 2006/0149268 A1 * | 7/2006 | Truckai | .............. | A61B 17/1642 606/79 |
| 2006/0276816 A1 * | 12/2006 | Eckman | ......... | A61B 17/320708 606/160 |
| 2012/0271357 A1 * | 10/2012 | Arthur | ............... | A61B 17/1617 606/279 |
| 2012/0330314 A1 * | 12/2012 | Schaller | ............. | A61B 17/7094 606/79 |
| 2014/0058394 A1 * | 2/2014 | Siegal | ................ | A61B 17/1631 606/80 |
| 2014/0100574 A1 * | 4/2014 | Bono | ................. | A61B 17/1615 606/80 |
| 2015/0313615 A1 * | 11/2015 | Jacobson | ........... | A61B 17/1659 606/85 |
| 2019/0350598 A1 * | 11/2019 | Jacobson | ........... | A61B 17/1671 |

(Continued)

*Primary Examiner* — Matthew J Lawson

(57) ABSTRACT

The present disclosure provides a cutting tool for surgical procedures. More specifically, the present cutting tool is suitable for bi-directional cutting and removal of soft and hard tissues for surgical procedures. The cutting tool includes a substantially rigid shaft having a shaped end portion. The shaped end portion includes a plurality of shaped talons; each talon including a body bent to retain tissue, and each talon including a cutter end. The cutter end includes both acute and obtuse cutting surface relief angles for diverse cutting action with respect to hard and soft tissues.

17 Claims, 4 Drawing Sheets

(56) References Cited

U.S. PATENT DOCUMENTS

| | | | | |
|---|---|---|---|---|
| 2020/0046377 A1* | 2/2020 | Woodard | ............ | A61B 17/1604 |
| 2022/0125444 A1* | 4/2022 | Frock | ................. | A61B 17/7062 |
| 2022/0249103 A1* | 8/2022 | Bono | ................. | A61B 17/1659 |

* cited by examiner

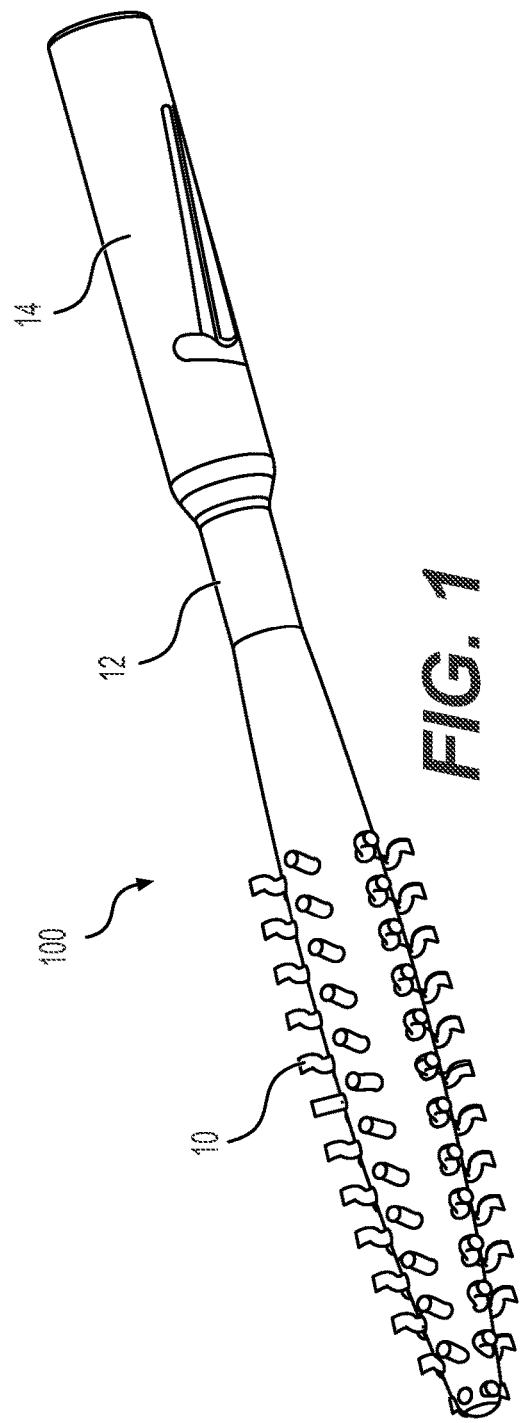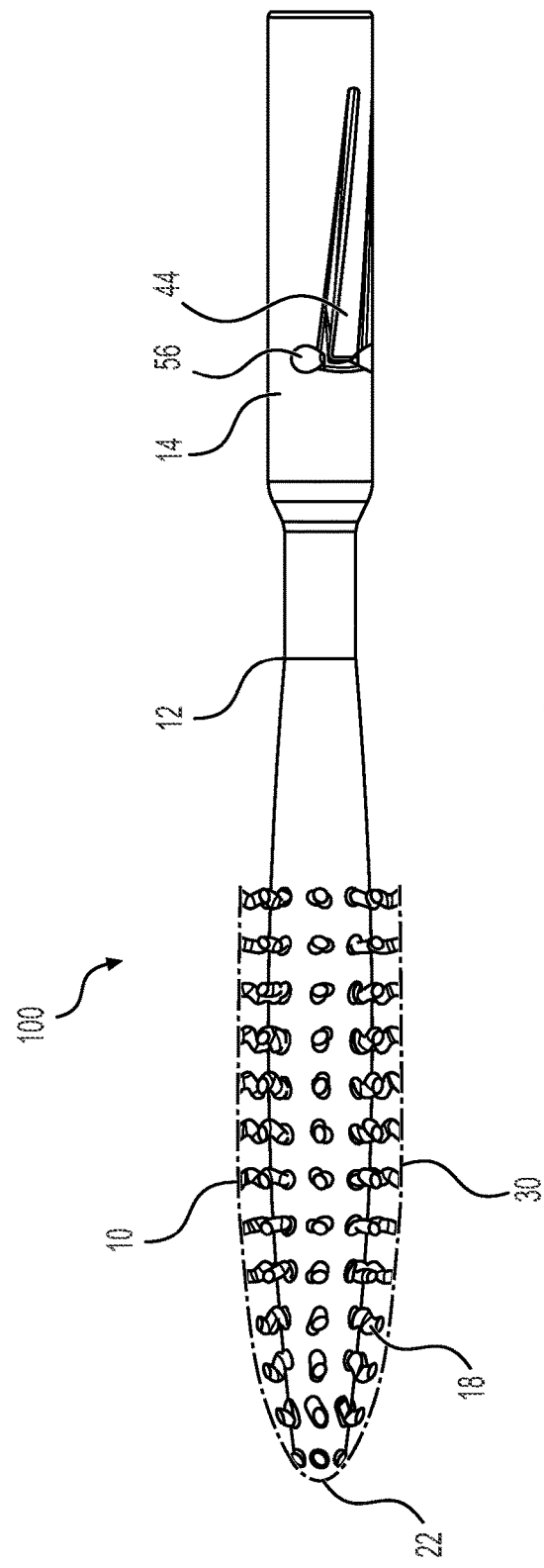

BI-DIRECTIONAL DISK REMOVAL AND DECORTICATION TOOL

PRIORITY CLAIM

In accordance with 37 C.F.R. 1.76, a claim of priority is included in an Application Data Sheet filed concurrently herewith. Accordingly, the present application claims priority to U.S. Provisional Patent Application No. 63/180,444, titled "BI-DIRECTIONAL DISK REMOVAL AND DECORTICATION TOOL", filed Apr. 27, 2021. The contents of the above referenced application are incorporated herein by reference in their entirety.

FIELD OF DISCLOSURE

The present disclosure generally relates to surgical tools for spinal procedures and, more particularly, to a tool that can be oscillated or rotated in both directions about the longitudinal centerline of the cutting tool to remove spinal disk material as well as decortication of bone.

BACKGROUND INFORMATION

In the treatment of spinal issues, such as vertebral displacement, spodylosis, spondylolisthesis, spondylitis, rotation of the vertebrae, segmental instability, disc degeneration, fractures, congenital defects, and tumors, it is common for the surgeon to denude, decorticate and shape the host bone to develop a disk space to insert an intervertebral implant, as well as apply graft bone in and around the implant. In order to achieve bone fusion or osteogenesis, there must be a bone to bone contact between the host bone and the bone graft. To achieve such a contact surface, soft tissue normally found on bone, such as periosteum, muscle, ligament and fibrous tissue, must be removed from the contact point of both the host and graft bone. Therefore, in addition to meeting the requirements to remove soft tissue from bone, surgeons are often required to remove some of the cortical bone layer from the bone graft site and/or the bone graft.

Typically, curettes, scrapers or other hand operated filing instruments are used for osteophyte resection, and chisels or drills are used for removing bone cortical tissue. These devices are difficult to move a sufficient distance to be effective in removing the soft tissue material. When material is removed, the surfaces are typically rounded and bell-mouthed due to the tool traveling the farthest at the edge of the bone surface and the inability to hold the tool absolutely steady. Conventional decortication systems are also limited. In particular, when decorticating with a chisel or drill, substantially all of the cortical tissue is removed during the procedure. It would instead be preferable to provide an oscillating decortication tool operable to allow the surgeon to determine the amount of soft and hard materials removed from the vertebral endplates and bones.

It has been well documented in the clinical literature that soft tissue significantly slows, if not totally prevents, the connection of bone cells to complete bone fusion when obstructed by the presence of soft tissue. Slowing the growth of the bone cells may cause the fusion procedure to fail, thereby resulting in a negative impact on the health of the patient.

An additional drawback relates to when the decortication is being performed with instruments which do not provide a means to control the amount of cortical bone being removed. With little control of the bone removal process, surgeons can often take too much or too little cortical bone, which leads to different surgical results.

Finally, there are ergonomic needs that a disc and decortication tool must satisfy in order to achieve acceptance by the end user. The cutting tool must be easily and quickly assembled to a motorized oscillating tool using minimal hardware and requiring a minimal number of tools. Further, the cutting tool should not require excessive strength or require a foot to be used as a lever to force the tool into the bone with sufficient force to remove the desired tissue. Still yet, the tool should be self-cleaning with respect to cleaning tissue from the cutting tool to reduce the time required for the surgery and lower the workload on the surgeon and nurses.

Thus, the present disclosure provides a cutting tool that cuts when oscillated in both directions around the longitudinal centerline of the cutting tool. The cutting tool also is suitable for removal of soft and hard tissues. Still yet, the cutting tool is constructed to retain and hold tissue in the surgical site and self-clean tissue from the cutting tool when removed from the surgical site and oscillated or rotated.

SUMMARY OF THE DISCLOSURE

Briefly, the disclosure provides a cutting tool for surgical procedures on mammals. More specifically, the present cutting tool is suitable for bi-directional cutting and removal of soft and hard tissues for surgical procedures. The cutting tool includes a substantially rigid shaft having a shaped end portion. The shaped end portion includes a plurality of shaped talons; each talon including a body bent to retain tissue, and each talon including a cutter end. The cutter end includes both acute and obtuse cutting surface relief angles for diverse cutting action with respect to hard and soft tissues.

Accordingly, it is an objective of the present disclosure to provide a bi-directional surgical cutting tool for hard and soft tissue materials.

It is a further objective of the present disclosure to provide a bi-directional surgical cutting tool which provides a cutting action when rotated either direction or oscillated about the longitudinal centerline of the cutting tool.

It is yet a further objective of the present disclosure to provide a bi-directional surgical cutting tool having a plurality of cutting talons secured to an outer surface of the cutting body.

It is another objective of the instant disclosure to provide a cutting talon that includes a range of relief angles from the cutting surface to cooperate with various hardness materials.

It is still another objective of the present disclosure to provide a cutting talon that is suitable to retain cut material on the cutting tool for removal from the surgical site, the cutting tool self-cleaning once removed from the surgical site with rotation or oscillation.

Still yet another objective of the present disclosure is to provide a talon construction that includes a series of bends to provide rigidity and controlled flex of the talon during operation.

Other objectives and advantages of this disclosure will become apparent from the following description taken in conjunction with the accompanying drawings wherein are set forth, by way of illustration and example, certain embodiments of this disclosure. The drawings constitute a part of this specification, include exemplary embodiments of the present disclosure, and illustrate various objects and features thereof.

BRIEF DESCRIPTION OF THE FIGURES

FIG. 1 is a top front perspective view of one embodiment of a bi-directional cutting tool for removing disk and hard tissues;

FIG. 2 is a side view of the bi-directional cutting tool;

DETAILED DESCRIPTION OF THE PREFERRED EMBODIMENTS

Figure 3:
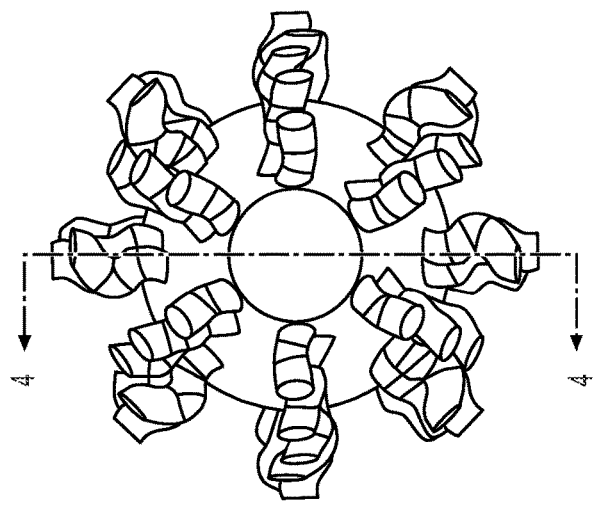
FIG. 3 is a front view of the embodiment shown in FIG. 1.
Figure 4:
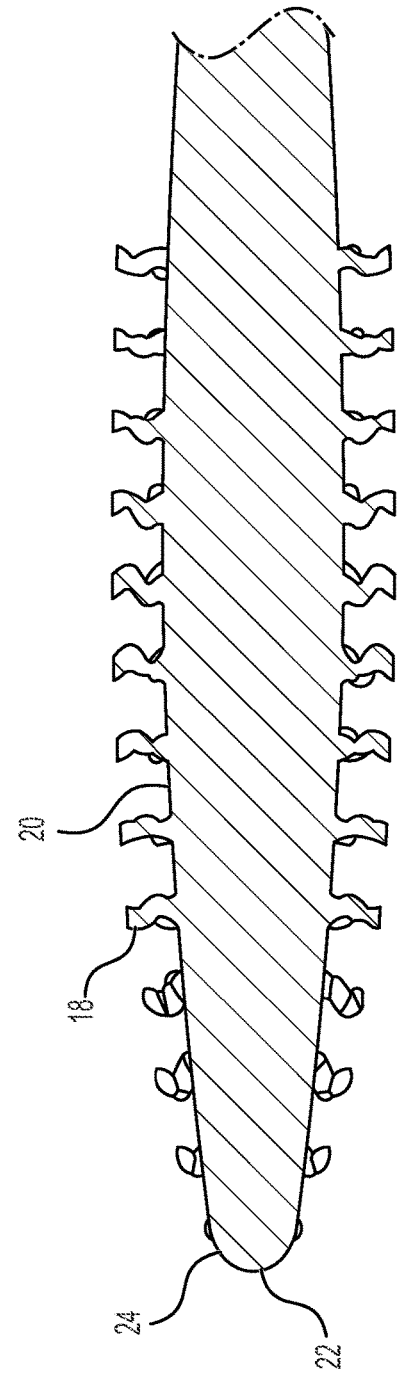
FIG. 4 is a section view taken along lines 4-4 of FIG. 3.
Figure 5:
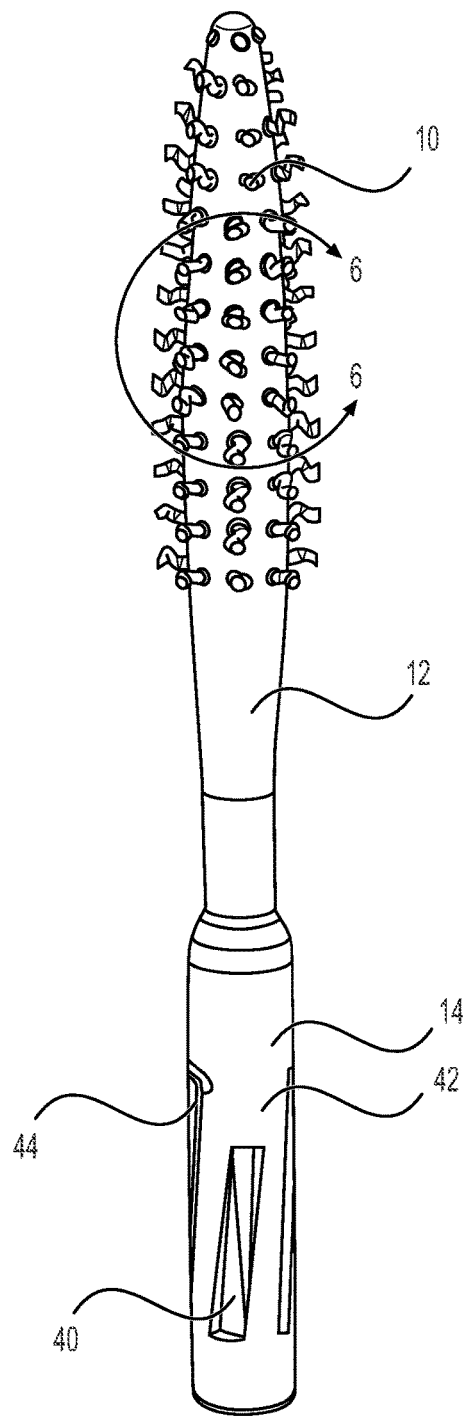
FIG. 5 is a front side perspective view of the embodiment shown in FIG. 1.
Figure 6:
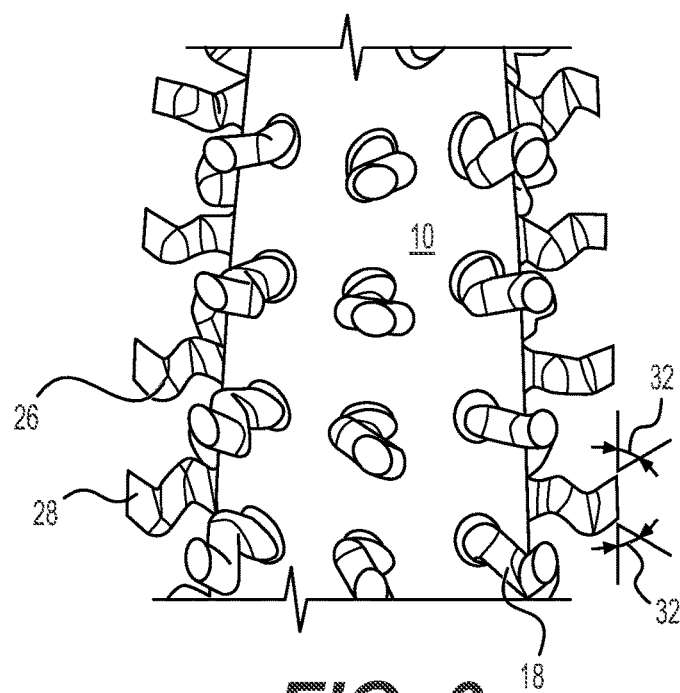
FIG. 6 is a partial view taken along lines 6-6 of FIG. 5 illustrating the cutting edges provided by the talons.

While the present disclosure is susceptible of embodiment in various forms, there is shown in the drawings and will hereinafter be described a presently preferred embodiment with the understanding that the present disclosure is to be considered an exemplification of the disclosure and is not intended to limit the disclosure to the specific embodiments illustrated.

Figure 7:
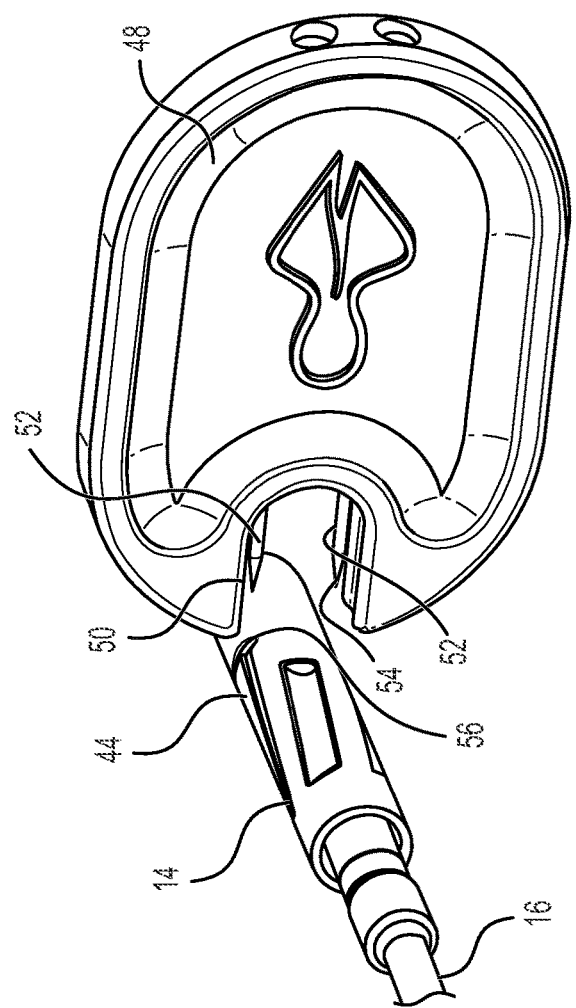
FIG. 7 is a partial perspective view illustrating a removal tool for removing the bi-directional cutting tool from the shank of the oscillating tool.
Figure 8:
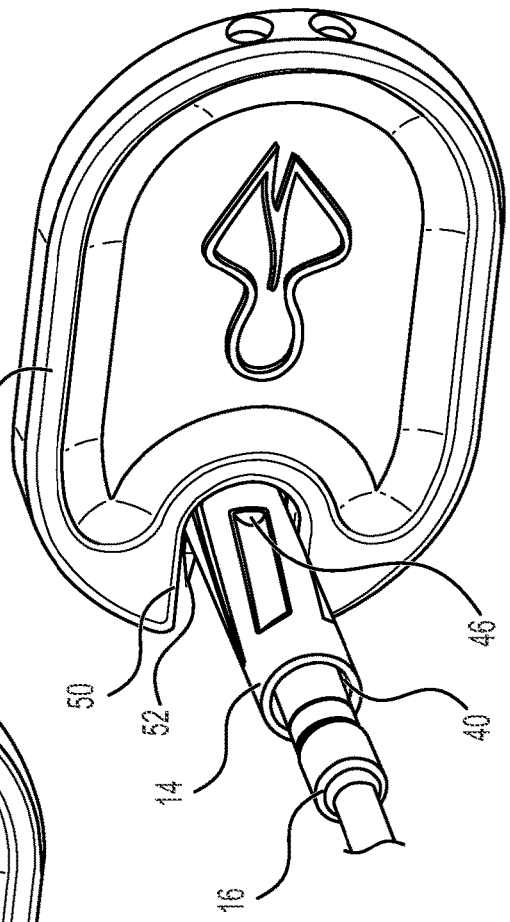
FIG. 8 is a partial perspective view illustrating a removal tool for removing the bi-directional cutting tool from the shank of the oscillating tool.

Referring generally to FIGS. 1-8, a bi-directional cutting tool 100 for disc and bone removal and modification is illustrated. The bi-directional cutting tool 100 includes a shaped head portion 10 and a shank portion 12. In some embodiments, the shank portion 12 includes a connector 14 for quick connection to and release from the driving shaft 16 of the oscillating tool (FIGS. 7-8). In the preferred embodiment, the shaped head portion 10 includes a "flame" or "tree" shape as is known in the art of tool making. The flame or tree shape generally includes one or more blended radii 20 that intersect to form the flame or tree shape. The distal end 22 of the shaped head portion 10 includes a spherical radius 24 devoid of talons or cutting surfaces to prevent drilling into the bone with the bi-directional cutting tool 100 configured for disk removal and decortication. Other embodiments may include talons or bi-directional cutting surfaces at the distal end 22 for drilling, bone shaping, and the like. It should also be noted that while the preferred embodiment for disk removal and decortication includes the flame or tree shape, tapered, straight, ball and other suitable shapes may be utilized for other surgical procedures without departing from the scope of the disclosure.

Attached to, or more preferably integral to, the shaped head portion 10 is a plurality of talons 18. The talons 18 are generally constructed and arranged to cut and grab the disk material which is held against the shaped head portion 10 and the distal ends of the talons 18. This construction allows the disk material to be removed from the surgical site by removing the tool. The construction of the talons 18 also allows self-cleaning of the tool by high speed oscillation or rotation once removed. This allows the tool to be quickly cleaned for reuse in removing more disk material, and eliminates the need for tool changes each time the tool is filled with disk material. Once the disk material is removed, the talons 18 can be utilized to decorticate the bone. Thus, the same tool can be utilized to remove disk material and decorticate and shape the bone. In order to facilitate the broad spectrum of uses, the talon 18 includes a unique structure. The talon 18 in the preferred embodiment is round in cross-section and includes one or more bends 26 terminating in a generally flat cutting surface 28; the cutting surface 28 being substantially parallel to the surface of the shaped head portion 10. The bends 26 provide rigidity and controlled flex to the talon 18. In addition, because one of the bends in the talon 18 is provided in proximity to the outer cutting surface 30, while the cutting surface 28 is oriented parallel to the shaped head portion 10, various relief angles 32 are provided all around the cutting surface 28. This construction allows the same talon 18 to cut, scrape and smooth the surface being cut while talons rotationally oriented at different angles around and along the bi-directional cutting surface 30 contact the bone surface. The side of the talon 18 having higher relief angles 32 reduces load on the talon 18, and allows higher material removal with the same load, while the lower relief angles 32 scrape and/or rub the surface to leave a relatively smooth surface finish. This construction allows the same tool to be used for roughing and finishing of the bone surface and provides a suitable surface for supporting implants and promoting bone growth. It should be noted that the term "substantially" in this context means within manufacturing tolerances. The talon bends 26 are preferably about ninety degrees, and each talon 18 preferably includes two bends 26 along its length. The term "about" is defined herein as within manufacturing tolerances. However, it should be noted that other bend angles, and as few as one bend, and as many as six, may be utilized without departing from the scope of the disclosure. The bends may be axially aligned with each other along the length of each talon 18, or there may be a rotation between the bends to provide for more or less flexion of the talon during operation for smoother surface finish or faster material removal respectively. The preferred material for the bi-directional cutting tool 100 is printed titanium. However, other materials including high speed steel, stainless steel, carbide and the like, may be utilized without departing from the scope of the disclosure. Suitable coatings may also be utilized on the outer surface of the bi-directional cutting tool 100 to reduce friction and increase surface hardness; such coatings may include, but should not be limited to, titanium nitride, titanium carbide, chromium carbide, titanium carbonitride and the like.

Referring to FIGS. 1, 2, 5, 7 and 8, the connector 14 is illustrated as secured or integrally formed as a portion of the shank 12. The driving shaft 16 of the oscillating tool may be a hard shaft (as illustrated), or alternatively may include a chuck, collet or cable drive without departing from the scope of the disclosure, so long as the driving shaft 16 is suitably coupled to the bi-directional cutting tool 100 to prevent slippage between the driving shaft 16 and the bi-directional cutting tool 100 during use. The connector 14 of the preferred embodiment is constructed to be hollow, having an internal cavity 40 sized to closely fit over the distal end of an oscillating driving shaft 16; the hollow portion 42 having at least one, and more preferably a plurality of spring tabs 44. The spring tabs 44 are biased to extend inwardly into the hollow portion 42, so that when the bi-directional cutting tool 100 is slipped over the driving shaft 16, the spring tabs 44 engage notches or rings 46 on the driving shaft 16 to prevent the bi-directional cutting tool 100 from separating from the driving shaft 16 during use. A removal tool 48 may be used to remove the bi-directional cutting tool 100 from the driving shaft 16 when desired. The removal tool 48 preferably includes a U-shaped throat 50 sized to pass over the diameter of the connector 14. Positioned within the throat 50 are one or more pins 52. The pins 52 each include a spire end 54 sized to cooperate and enter a tunnel 56 provided in the connector 14, which allows the spire end 54 to extend under a respective spring tab 44 to lift the spring tab out of contact with the notches 46 to allow the bi-directional cutting tool 100 to be removed from the driving shaft 16. In this manner, reassembly merely requires the connector portion 14 of the bi-directional cutting tool 100 to be slipped over the driving shaft 16 and pushed into position so that the spring tabs 44 re-engage the driving shaft 16 to lock the cutting tool 100 in position for work. The removal tool 48 may be constructed of any suitable material, including plastic, metal, resin, or any suitable combination thereof. In a most preferable embodiment, the removal tool 48 is constructed from a material or combination of materials that are suitable to withstand autoclave cleaning.

It is to be understood that while a certain form of the disclosure is illustrated, it is not to be limited to the specific form or arrangement herein described and shown. It will be apparent to those skilled in the art that various changes may be made without departing from the scope of the disclosure, and the disclosure is not to be considered limited to what is shown and described in the specification and any drawings/figures included herein.

One skilled in the art will readily appreciate that the present disclosure is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the disclosure and are defined by the scope of the appended claims. Although the disclosure has been described in connection with specific preferred embodiments, it should be understood that the disclosure as claimed should not be unduly limited to such specific embodiments. Indeed, various modifications of the described modes for carrying out the disclosure, which are obvious to those skilled in the art, are intended to be within the scope of the following claims.

What is claimed is:

1. A bi-directional cutting tool for removal of hard and soft biological material comprising:
   a shaped head portion and a shank portion, attached to the shaped head portion is a plurality of talons, the talons constructed and arranged to cut and grab disk material which is held against the shaped head portion and distal ends of the talons, each of the talons including a plurality of bends and terminating in a generally flat cutting surface, the cutting surface being substantially parallel to an exterior surface of the shaped head portion, wherein the disk material is removed from the surgical site by removing the cutting tool,
   wherein at least one of the bends is provided in proximity to the cutting surface so that the distal end of each talon is positioned at an angle with respect to a longitudinal centerline of the bi-directional cutting tool, so that various relief angles are provided around the cutting surface.

2. The bi-directional cutting tool for removal of hard and soft biological material as claimed in claim 1 wherein the talons are round in cross-section.

3. The bi-directional cutting tool for removal of hard and soft biological material as claimed in claim 1, wherein the bends are constructed and arranged to provide rigidity and controlled flex to the talon.

4. The bi-directional cutting tool for removal of hard and soft biological material as claimed in claim 1, wherein higher relief angles reduce load on the talon and allows higher material removal with the same load, while lower relief angles scrape and/or rub the surface to leave a relatively smooth surface finish.

5. The bi-directional cutting tool for removal of hard and soft biological material as claimed in claim 1, wherein the talon bends are about ninety degrees, and each talon includes two bends along its length.

6. The bi-directional cutting tool for removal of hard and soft biological material as claimed in claim 1, wherein the bends are axially aligned with respect to each other along the length of each talon.

7. The bi-directional cutting tool for removal of hard and soft biological material as claimed in claim 1, wherein the bends are rotated with respect to each other to provide for more or less flexion of one talon with respect to the next talon.

8. The bi-directional cutting tool for removal of hard and soft biological material as claimed in claim 1, wherein the shaped head portion is a flame shape.

9. The bi-directional cutting tool for removal of hard and soft biological material as claimed in claim 1 wherein the shaped head portion is a tree shape.

10. The bi-directional cutting tool for removal of hard and soft biological material as claimed in claim 1, wherein a distal end of the shaped head portion includes a spherical radius devoid of talons and of any cutting surface.

11. The bi-directional cutting tool for removal of hard and soft biological material as claimed in claim 1, wherein a distal end of the shaped head portion includes talons or bi-directional cutting surfaces for drilling and bone shaping.

12. The bi-directional cutting tool for removal of hard and soft biological material as claimed in claim 1, wherein bi-directional cutting tool is constructed of printed titanium.

13. The bi-directional cutting tool for removal of hard and soft biological material as claimed in claim 1, wherein the shank portion includes a connector for quick connection to and release from a driving shaft.

14. The bi-directional cutting tool of claim 1, wherein each talon is a single integrally formed material.

15. The bi-directional cutting tool of claim 14, wherein each talon is made of titanium material.

16. The bi-directional cutting tool of claim 1, wherein the bends of each talon are axially aligned with each other along the length of the talon.

17. The bi-directional cutting tool of claim 1, wherein:
   each talon is a single integrally formed material; and
   the bends of each talon are axially aligned with each other along the length of the talon.

* * * * *